United States Patent [19]

Lehmann

[11] Patent Number: 5,528,040
[45] Date of Patent: Jun. 18, 1996

[54] RING-DOWN CAVITY SPECTROSCOPY CELL USING CONTINUOUS WAVE EXCITATION FOR TRACE SPECIES DETECTION

[75] Inventor: Kevin K. Lehmann, Lawrenceville, N.J.

[73] Assignee: Trustees of Princeton University, Princeton, N.J.

[21] Appl. No.: 335,052

[22] Filed: Nov. 7, 1994

[51] Int. Cl.⁶ .................................................... G01N 21/17
[52] U.S. Cl. .......................................... 250/343; 356/439
[58] Field of Search ............................. 250/343; 356/439

[56] References Cited

U.S. PATENT DOCUMENTS 5,026,991   6/1991   Goldstein et al. ...................... 250/343

OTHER PUBLICATIONS

Trautmann et al., "Determination of the Deuterium Abundance in Water using a CW Chemical DF Laser", Appl. Phys., 24, No. 1, 1981, pp. 49–53.
J. White, Long Optical Paths of large Aperture, 32 *J. Opt. Soc. Amer.*, 285 (May, 1942).
D. Herriott et al., Off–Axis Paths in Spherical Mirror Interferometers, 3 *Appl. Opt.* (4), 523 (Apr., 1964).
A. O'Keefe & D. Deacon, Cavity ring–down optical spectrometer for absorption measurements using pulsed laser sources, 59 *Rev. Sci. Instrum.*, 2544 (Dec., 1988).
D. Romanini & K. Lehmann, Ring–down cavity absorption spectroscopy of the very weak HCN overtone bands with six, seven, and eight stretching quanta, 99 *J. Chem. Phys.* (9), 6287 (Nov. 1, 1993).
B. Dahmani et al., Frequency stabilization of semiconductor lasers by resonant optical feedback, 12 *Opt. Letter* (11), 876 (Nov. 1987).
C. Tanner et al., Atomic beam collimation using a laser diode with a self–locking power–buildup cavity, 13 *Opt. Letter* (5), 357 (May, 1988).

G. Rempe et al., Measurement of ultralow losses in an optical interferometer, 17 *Opt. Letters* (5), 363 (Mar. 1, 1992).
T. Yu & M. Lin, Kinetics of Phenyl Radical Reactions Studied by the "Cavity–Ring–Down" Method, 115 *J. Am. Chem. Soc.*, 4371 (1993).
G. Meijer et al., Coherent cavity ring down spectroscopy, 217 *Chemical Physics Letters* (1,2), 112 (Jan. 7, 1994).
J. Scherer et al., Cavity ring down dye laser spectroscopy of jet–cooled metal clusters: $CU_2$ and $CU_3$, 172 *Chemical Physics Letters (3,4)*, 214 (Sep. 7, 1990).
D. Cooper & R. Martinelli, Near–infrared diode lasers monitor molecular species, *Laser Focus World*, 133 (Nov., 1992).
F. Stoelkel & G. Atkinson, Time evolution of a broadband quasi–cw dye laser: limitations of sensitivity in intracavity laser spectroscopy, 24 *Applied Optics* (21), 3591 (Nov. 1, 1985).
K. Lehmann & D. Romanini, Molecules in the Stellar Environment, *Experimental Measurement of Weak Band Intensities in Molecules in the Stellar Environment*, (Springer, 1994).

Primary Examiner—Carolyn E. Fields
Assistant Examiner—Edward J. Glick
Attorney, Agent, or Firm—Ratner & Prestia

[57] ABSTRACT

An apparatus for detection and measurement of trace species in a sample gas. A ring down cavity cell is filled with the sample gas. A continuous wave laser emits radiation, which is directed from the continuous wave laser to the ring down cavity cell where it resonates. A photodetector measures radiation levels resonated by the ring down cavity cell and produces a corresponding signal. The decay rate of the ring down cavity cell is calculated from the signal produced by the photodetector and is used to determine the level of trace species in the sample gas.

26 Claims, 1 Drawing Sheet

RING-DOWN CAVITY SPECTROSCOPY CELL USING CONTINUOUS WAVE EXCITATION FOR TRACE SPECIES DETECTION

FIELD OF THE INVENTION

This invention relates generally to absorption spectroscopy and, in particular, is directed to a trace species detection apparatus combining a Ring Down Cavity (RDC) cell and a continuous laser light source.

BACKGROUND OF THE INVENTION

In many industrial processes, the concentration of trace species in flowing gas streams must be measured and analyzed with a high degree of speed and accuracy. Such measurement and analysis is required because the concentration of contaminants is often critical to the quality of the end product. Gases such as $N_2$, $O_2$, $H_2$, Ar, and He are used to manufacture integrated circuits, for example, and the presence in those gases of impurities such as water—even at parts per billion (ppb) levels—is damaging and reduces the yield of operational circuits.

Consequently, many complex and sophisticated devices are available for measuring trace species in gases. They seek to detect low levels, on the order of a few parts per billion (ppb) by volume or less, with a short response time. As an example, electrochemical cells are used commercially to detect and monitor water contamination in high-purity process gas streams. These cells are limited in sensitivity to water levels around 30 ppb, have a relatively long response time, are poisoned by high transient concentrations of water, and are subject to interferences from other molecules.

I. Absorption Spectroscopy

Absorption spectroscopy offers higher sensitivity, response times on the order of microseconds, immunity from poisoning, and limited interference from other molecular species. Various molecular species, but especially simple molecules such as water, can be detected or identified by absorption spectroscopy. Thus, absorption spectroscopy provides a general method of detecting important trace species. In the gas phase, the sensitivity and selectivity of this method is optimized because the species have their absorption strength concentrated in a set of sharp rotational lines. Water is particularly suitable for absorption spectroscopy because the molecule has large rotational constants leading to a relatively small rotational partition function ($q_{rotation}$=43 at room temperature). The narrow lines in the spectrum can be used to discriminate against most interfering species.

The relatively high sensitivity with which water can be spectroscopically monitored is important to manufacturers of high-purity gases used in the semiconductor industry. In most instances, parts per million (ppm) level detection is readily obtained. Detection sensitivities at the ppb level are attainable, in some cases, for water. Accordingly, several spectroscopic methods have been applied, including absorption measurements in traditional long pathlength cells, photoacoustic spectroscopy, frequency modulation spectroscopy, and intracavity loss spectroscopy. These methods have several features, to be discussed below, which make them difficult to use and impractical for industrial applications. They have been largely confined, therefore, to laboratory investigations.

The sensitivity of absorption-based methods is limited by the smallest effective sample absorption coefficient that can be measured. This in turn is limited by two factors: the noise equivalent fractional change in sample transmission and the effective pathlength through the sample. A single pass through the sample is limited by the physical dimensions of the apparatus, and is typically on the order of 0.1 to 1 meters.

A. Traditional Long-Path Spectroscopy

The traditional approach to increasing the absorbance pathlength (by on the order of 10–100 times) is to use a multipass cell to fold the light path many times through the cell. The most important design is that first reported by J. White, *Long Optical Paths of Large Aperture*, 32 J. Optical Soc'y Am. 285 (May 1942). Although many modifications of the original design have been published, White's original design is based upon three mirrors. A key feature of all the designs is the use of low F number optics (the F number is the ratio of the focal length to the limiting aperture of an optical system; the light throughput of such a system is proportional to $1/F^2$) and a placement of the mirrors at a separation that is on the edge between a stable and unstable optical cavity.

Both multipass cells and lasers can be treated as optical cavities which confine light with a certain loss per pass. Cavities are stable or unstable depending on the behavior of light rays slightly divergent from the optical axis of the cavity. These will remain close to the axis if the cavity in which they propagate is stable; in an unstable cavity, their distance from the axis will diverge exponentially. For a cavity on the edge between stable and unstable, the divergence is linear with the number of passes. Light is mode-matched into a cavity if the light beam has the right size and wavefront to exactly overlap itself on each round trip of the cavity.

The use of focusing optics at the edge between stable and unstable configurations results in a refocusing to a constant spot size on each round trip through the White cell and a running line of spots on one mirror. The pathlength is adjusted by changing the number of spots that fall on this mirror. Large mirrors are needed both to keep the light throughput high when such a cell is used with incoherent sources and to give ample space to resolve the spots used for coupling the light into and out of the cell. The maximum number of traversals of the cell is limited by both the reflectivity of the mirrors and by the need to physically separate the spots. Practical limits have been on the order of a few hundred passes of the cell, which translates to a maximum pathlength on the order of 0.5 km for cells of a few meters in physical length.

Special, very large cells have been constructed that allow pathlengths of several kilometers to be reached. These large cells are expensive, however, and difficult to control in temperature. Because they are not stable optical cavities, density gradients and turbulence caused by convective flow can easily destroy the optical beam quality and lead to substantial noise in the optical transmission. This is particularly a problem when the cells are used with Fourier Transform instruments, but also limits the sensitivity when used with coherent sources.

In recent years, novel cell designs based upon off-axis coupling into a marginally stable, near concentric optical cavity have been used. These designs are known as Herriott cells. D. Herriott et al., *Off-Axis Paths in Spherical Mirror Interferometers*, 3 Applied Optics 523 (April 1964). Light enters and leaves the cell through a single hole in one of the two mirrors. Unless the input light is carefully mode-matched, the spot size changes on each round trip, but it returns to its original size when it once again passes through the coupling hole.

The stable optical cavity makes the cell less sensitive to both mechanical vibration and convection than a White cell. One drawback is that the pathlength is varied by scanning the physical separation of the two mirrors and this can be somewhat difficult in a vacuum system. The effective F number of a Herriott cell is much greater than a White cell and, therefore, Herriott cells are not as efficient for incoherent sources. For laser sources, however, Herriott cells are superior. Like White cells, the maximum pathlength of the Herriott cell is limited by both the finite reflectivity of the large mirrors required (the beam attenuation through the cell is proportional to the mirrors' reflectivity raised to the power of the number of cell traversals) and by the requirement that, at each round trip, the beam forms a distinct, spatially resolved spot on one of the mirrors. For cells of practical size, these factors limit the total pathlengths to about 1 km or less.

B. Photoacoustic Spectroscopy

Photoacoustic or optoacoustic spectroscopy monitors absorption by its effect on the sample and, therefore, like laser induced fluorescence, is an indirect detection method. Following absorption of laser light, molecules collisionally relax, releasing heat which increases the local temperature. This local temperature rise leads to expansion, followed by contraction, as the heat energy is dissipated. Thus, by chopping a laser beam at an acoustical frequency (about 1 KHz), a synchronous sound wave will be produced which can be detected by a microphone. Photoacoustic cells are built to minimize sound waves produced by window absorption and may include a resonant inner section which allows the formation of acoustic standing waves at the laser chopping frequency. Microphones are extremely sensitive and, with a careful cell design, allow detection on the order of $10^{-8}$ W/cm of deposited energy. Because the deposited energy is measured, the signal (and thus the sensitivity) increases linearly with average laser power.

Consequently, photoacoustic spectroscopy is typically done with the sample cell inside the optical cavity of a 100% amplitude modulated, continuous wave laser to maximize the signal strength. A minimum noise equivalent absorption coefficient of $4 \times 10^{-10}$ cm$^{-1}$ has been obtained in this way. Efficient conversion of the heat to acoustic energy requires pressures of at least 10 to 100 torr, but this can be made up principally of buffer gas when the sample vapor pressure is too low.

The principal advantage of photoacoustic spectroscopy is its extreme sensitivity, the highest so far obtained for species that do not fluoresce. A number of drawbacks of photoacoustic spectroscopy are: (1) a quiet acoustic environment is required (therefore, use of an electric discharge or rapid flow of the sample leads to a substantial increase in noise); (2) the sample is exposed to high average light flux, which can lead to photochemistry in some situations; and (3) the indirect nature of the detection makes determination of absolute absorption strengths difficult. The only practical way to calibrate the strength of the acoustic signal is to use a mixture of a gas which has some transition whose cross-section is already known along with the gas of interest. Even with such calibration, uncertainties on the order of 20% remain.

C. Intracavity Loss Absorption Spectroscopy

A dye laser uses a solution of an organic dye that is optically pumped by another laser to produce gain. The principal advantage of these lasers is that they can be tuned over a broad spectral region. Dye lasers have a large gain bandwidth (the gain bandwidth is the spectral region over which a laser has net gain on each round trip).

When a laser with a large gain bandwidth is switched on, light intensity builds up from spontaneous emission. At first, the spectrum matches the gain bandwidth of the laser. The spectrum then begins to shift and narrow due to gain narrowing and then mode competition. If the laser contains a weak intracavity (i.e., inside the optical cavity) absorber, whose absorption features are narrow compared to the laser bandwidth, then as the time during which the laser has been pumped ($t_g$) increases, narrow "holes" are eaten out of the broadband laser emission spectrum.

It has been established that, for the first 500 microseconds, the strength of these holes have an equivalent absorbance, A, of $A = \alpha \times f \times c \times t_g$, where $\alpha$ is the absorbance coefficient of the gas, f is the fraction of the laser cavity filled by the absorber (typically about 0.5), and c is the speed of light. Thus, the effective pathlength, $L_{effective}$, is given by: $L_{effective} = f \times c \times t_g$, which can be up to a maximum of 100 km. Beyond this generation time, $t_g$, mechanical vibrations and other sources of dephasing cause the depth of the absorption features to no longer follow a simple Lambert-Beer's law. See F. Stoeckel & G. Atkinson, *Time Evolution of a Broadband Quasi-cw Dye Laser: Limitations of Sensitivity in Intracavity Laser Spectroscopy*, 24 Applied Optics 3591 (Nov. 1985). Timing is achieved by the use of acoustooptic modulators on the pump and output of the laser, and the laser output is dispersed on a large spectrograph with an array detector. Using this technique, it is possible to measure spectroscopic features with an absorption coefficient as low as a few times $10^{-8}$ cm$^{-1}$.

The sensitivity of this method is not quite as high as photoacoustic spectroscopy, but is much higher than that obtained with traditional long path cells. As long as one is careful to remain in the early time region, the absorption coefficient and, thus, the cross-section (assuming one knows the gas density and cavity fill factor), can be extracted from the optical depth of the observed absorption features. Because of the pulsed nature of the experiment, and the near threshold operation of the laser, chances for inadvertent photochemistry are reduced as compared to intracavity photoacoustic spectroscopy. The chief disadvantage is that this method requires complex instrumentation. A custom-designed, continuous wave dye laser must be used that has been carefully designed to remove all sources of stray interference which can lead to narrow bandwidth spikes on the laser output spectrum. In order to achieve Doppler limited resolution, the method requires a spectrograph of extremely high dispersion (about $10^6$) (a dimensionless number customarily defined as $\Delta\lambda/\lambda$, where $\Delta\lambda$ is the smallest change in wavelength that can be measured), which is an expensive piece of custom instrumentation.

D. Ring-Down Cavity Spectroscopy

The current "standard" way to use absorption spectroscopy to detect trace species in the gas phase to frequency modulate (FM) a laser source and detect a modulation of the amplitude of the laser radiation after passing through a sample gas. To increase sensitivity, a multiple pathlength cell is typically used. Although many designs exist, they are almost universally variants of two basic designs: the White and Herriott cells. As long as a weak laser source (where detector noise dominates) is not used, a ring-down cavity is superior in every respect over these designs.

In order to make sensitive absorption measurements, laser beam intensity fluctuations must be distinguished from molecular absorptions. This problem is particularly daunting for pulsed lasers whose shot-to-shot fluctuations are typically 5%. Although these fluctuations can be normalized out to some extent, absorptions on the order of $10^{-3}$ (dimensionless) are required to yield an observable signal.

A novel type of long pathlength cell, known as the ring down cavity (RDC) cell, was introduced as a sensitive gas phase direct absorption technique by A. O'Keefe & D. Deacon, *Cavity Ring-Down Optical Spectrometer for Absorption Measurements Using Pulsed Laser Source,* 59 Rev. Sci. Instrum. 2544 (Dec. 1988). This technique is based upon the measurement of the rate of absorption rather than the magnitude of absorption of a light pulse confined within a closed cell cavity. By measuring the decay time (i.e., the exponential time constant which describes the time-dependent probability for loss of a photon from the cavity modes of a stable resonator), the technique avoids the problems mentioned above encountered with pulsed lasers.

Ring down cavity spectroscopy is based upon a simple idea which has become practical due to recent advances in reducing loss in dielectric mirrors. A ring down cavity is made from two highly reflective, concave mirrors aligned in a near confocal geometry as a stable, low-loss optical cavity (i.e., the mirror separation, d, is less than twice the radius of curvature). It is now possible to purchase at low cost ($100 each) small mirrors with reflectivity R>99.99% over a range of some 60 nm anywhere in the visible spectrum, and mirrors with R=99.9998% have been reported near 840 nm (G. Rempe et al., *Measurement of Ultralow Losses in an Optical Interferometer,* 17 Optical Letters 363 (March 1992)).

Light from a conventional pulsed dye laser is coupled into the ring down cavity through one end. If the length of the laser pulse is less than the round trip time of the cavity (2d/c=10 to 20 nsec), then there can be no interference and a small but stable fraction of the incident light (about $10^{-5}$) enters the cavity. For a typical input pulse energy of a modest 1 mJ, this corresponds to about $3 \times 10^{10}$ photons. These photons are trapped between the high reflectivity mirrors and slowly decay (ring down) due to the combined loss of the mirrors and any molecular absorber located between the mirrors. The empty cell has a decay time, $\tau = d/c(1-R)$. On each round trip, a fraction of approximately $10^{-5}$ of the intracavity light intensity is transmitted through the back mirror and is detected by a photomultiplier tube (PMT) or some other sensitive photodetector. With the time constant of the PMT set long compared to the round trip time, its output current follows a smooth exponential decay. This curve can be digitized and a least squares fit to extract the decay rate.

Effective pathlengths as large as 70 km with a cell two meters long, near the maximum attained by the intracavity loss absorption spectroscopy (ICLAS) method, can be achieved using ring down cavity spectroscopy. Pathlengths of near 1000 km can be attained with the best reported commercial mirrors. Shot-to-shot fluctuations in the laser intensity are normalized out. Noise levels of about 0.005 ($2\sigma_s$), which corresponds to a noise equivalent absorption coefficient of about $8 \times 10^{-10}$ cm$^{-1}$, have been achieved. This is already quite competitive with the best that has ever been achieved by photoacoustic spectroscopy, and significantly better than the claimed sensitivity of ICLAS.

With mirrors of 1 ppm loss, a pathlength of 4000 km and noise equivalent absorption coefficient on the order of $10^{-12}$ cm$^{-1}$ should be attainable, which is orders of magnitude better than has ever been realized in any absorption-based detection method. At one atmosphere pressure, this corresponds to an absorption cross-section of $3 \times 10^{-32}$ cm$^2$. Because the method is based upon light traveling a known distance through a passive optical cavity, Lambert-Beer's law should hold quantitatively for all pathlengths, and thus the method provides a direct determination of the optical extinction coefficient at a known pathlength.

Compared with the other methods discussed above, ring down cavity spectroscopy is the simplest and least expensive to implement. A ring down cavity spectroscopy system can be implemented for a cost on the order of $5,000/unit, at least a factor of ten less than the ICLAS method (the extreme expense of the ICLAS method has prevented many laboratories from adopting it). It is also the most flexible. It is important to point out that the optics used are of such high reflectivity and modest cost because they are of small size; the coated surfaces are less than 1 cm in diameter. The method samples only a narrow pencil of the sample, with a cross-section less than 1 mm$^2$. Because a stable optical cavity is used, small deviations of the light beam due to density gradients will average out over several round trips, and should not contribute to noise as in traditional long pathlength cells. Furthermore, because the cross-sectional area of a ring down cell is much less than for a White cell, gas turbulence due to convection is much less likely to occur.

In summary, provided below is a list of some of the important advantages offered by the RDC cell over more traditional spectroscopic methods:

1) The RDC cell allows for much longer pathlengths. With both White and Herriott cells, practical considerations limit total pathlengths to about 100 times the physical length of the cell. With RDC cells, pathlengths of over $10^4$ times the physical length are easily achieved and, using the best reported commercially available mirrors, $(1-R) \approx 2$ ppm (where R=mirror reflectivity), pathlengths of $10^6$ times the cell length can be attained.

2) The RDC cell is sensitive only to absorption loss between the mirrors. With FM spectroscopy, one is sensitive to absorption and reflection losses throughout the optical pathlength. For the detection of a ubiquitous environmental component, such as water vapor, this is a very important distinction. The absorption of water vapor in the housing of the diode laser limits detection sensitivity. High vacuum ($<10^{-5}$ torr) would have to be maintained throughout the entire optical path in order for external water vapor not to dominate over a sample with 10 ppb of water vapor. Another difficulty with FM spectroscopy is weak interference effects due to reflections in the cell and mirrors, which produce modulations of the optical transmission on the order of 1 to 0.1 cm$^{-1}$, i.e., of the same characteristic width as absorption lines when broadened by atmospheric pressure.

3) The pathlength (and thus the concentration accuracy) of a RDC cell is much higher. In the RDC cell, pathlength is determined by measurements of time, which are easily made at an accuracy of 1 ppm or better. In a White or Herriott cell, pathlength is determined by a complex path of the light beam through the cell. A slight misalignment of the cell will change the number of passes through the cell and, thus, the pathlength. As the number of passes in the cell is increased, it is ever more difficult to know the exact pathlength inside the cell.

4) The RDC cell is much more compact. The light path inside the RDC cell is restricted to a Gaussian spot of less than 1 mm$^2$ cross-section. Thus, a narrow tube, of less than 1 cm$^2$ cross-section, can be used to contain the gas under study. In contrast, both White and Herriott cells use off-axis optical rays, and must have cross-sections on the order of 100 cm² or greater to realize long effective pathlengths. The reduced volume of the RDC means that much less of potentially hazardous chemicals need to be held in the cell, which would need to be flushed out to make a new measurement, to check the instrument with a calibration sample, or at the end of the day.

5) The RDC cell is much less sensitive to vibration and turbulence of gas inside the cell. A White cell is on the edge between a stable and unstable optical cavity. As a result, any deviation of a light ray, caused by either vibration of a mirror or index of refraction variation in the gas, will tend to accumulate on each pass, potentially producing a major source of noise. A Herriott cell is a marginally stable optical cavity and, therefore, has some averaging out of distortions, but as the pathlength is increased one moves closer to the edge of stability and the cell become more sensitive. The RDC is a near confocal cavity, and as such is the least sensitive of any optical design to misalignment and optical distortions.

6) FM spectroscopy is ultimately limited by the amplitude noise in the laser source. Typical near IR diode lasers have amplitude noise that is $10^2$ to $10^3$ above shot noise. In the RDC, the decay of a passive cavity is measured when the pump source is turned off. Thus, laser noise does not contribute and a detection sensitivity limited essentially only by shot noise is obtained. In view of the advantages outlined above, the present invention incorporates a ring down cavity cell.

II. Lasers

The term "laser" is an acronym for "light amplification by stimulated emission of radiation." As its name implies, a laser uses the principle of amplification of electromagnetic waves by stimulated emission of radiation. The essential parts of a laser are an amplifying medium, a source of pump power, and a resonator. The various types of lasers are classified according to their pumping or excitation mechanism: optically pumped lasers; gas-discharge lasers; pulsed gas lasers; chemical lasers; photodissociation lasers; nuclear lasers; gas-dynamic lasers; semiconductor lasers; free-electron lasers; and high-power, short-pulse lasers. A new type of laser is developed every year or so.

Lasers have rejuvenated spectroscopy because laser light far surpasses light from other sources in spectral or wavelength purity, intensity, coherence, and directionality (narrowness of beam). If required, laser light can be produced in extremely short and intense pulses. Lasers have increased the resolution and sensitivity of the conventional spectroscopic techniques discussed above.

Common commercial diode lasers, made from the III–V group of semiconductor materials, emit red and near-infrared wavelengths from about 0.63 to 1.55 μm. Diode lasers have been used for spectroscopic studies and monitoring of important molecular species, including water. Most of this work has been confined, however, to the laboratory. Near-IR diode lasers have the advantages of single-mode outputs of milliwatts, near room temperature operation, and high energy efficiency, in addition to the availability of fiberoptic technology and inexpensive auxiliary equipment such as low-noise current drivers, thermoelectric coolers, collimating lenses, detectors, and optical isolators. D. Cooper & R. Martinelli, *Near-Infrared Diode Lasers Monitor Molecular Species*, Laser Focus World (Nov. 1992).

One significant drawback of these devices is that they are available in only relatively narrow spectral regions. Most vendors are either unable or unwilling to wavelength-select diode lasers for spectroscopic applications. Another drawback to near-IR diodes is that only a limited number of molecular species have absorption features in the spectral region covered by these lasers. Nevertheless, many molecules of interest—including water—have near-IR absorption bands that are strong enough for detection at ppm and, in some cases, ppb levels. Given the utility of diode lasers for trace species detection, commercial sources of lasers designed for such applications are becoming available. In addition, new technology, such as quantum well lasers, are dramatically increasing the spectral coverage of diode lasers.

III. RDCS and Laser Sources

As discussed above, O'Keefe and Deacon pioneered ring down cavity spectroscopy in 1988. A. O'Keefe & D. Deacon, supra. They discussed prior work using direct precision absorption measurements and noted that such measurements require sophisticated optical systems and sources which have a stable output intensity. The required intensity stability was achieved using several types of continuous lasers (e.g., infrared lasers, diode lasers, and tunable cw dye lasers) frequency noise. O'Keefe and Deacon stated, "The same degree of success has not yet been possible for experimental systems based upon pulsed laser systems for several reasons."

Accordingly, O'Keefe and Deacon developed a technique (RDCS) which allows optical absorption measurements to be made using a pulsed light source and offers a sensitivity (absorption losses of about 1 ppm per pass can be detected by O'Keefe and Deacon) significantly greater than that attained using stabilized continuous light sources. They describe the "key to the successful operation of this technique for optical absorption measurements" as "the use of a laser pulse with a coherence length so short that no interference can become established in the test cavity." O'Keefe and Deacon specifically disclose an amplified pulsed dye laser to drive their system.

Since 1988, O'Keefe and others have demonstrated that the RDCS technique can be used to perform sensitive absorption spectroscopy in a molecular jet expansion. A. O'Keefe et al., *Cavity Ring Down Dye Laser Spectroscopy of Jet-Cooled Metal Clusters: $Cu_2$ and $Cu_3$*, 172 Chemical Physics Letters 214 (Sept. 1990). The technique uses pulsed laser sources. Others have used RDC cells for a spectroscopic study of the stretching overtones in HCN and established that it is of comparable sensitivity to photoacoustic spectroscopy. D. Romanini & K. Lehmann, *Ring-Down Cavity Absorption Spectroscopy of the Very Weak HCN Overtone Bands with Six, Seven, and Eight Stretching Quanta*, 99 J. Chem. Phys. 6287 (Nov. 1993). The study used a pulsed dye laser. Still other investigators have recently shown that RDCS also can be used for quantitative kinetics measurements. T. Yu & M. Lin, *Kinetics of Phenyl Radical Reactions Studied by the "Cavity-Ring Down" Method*, 115 J. Am. Chem. Soc. 4371 (1993). Again, a pulsed dye laser was used. Finally, RDCS was extended to UV light and to incorporate a long coherence length laser and a short cavity in order to obtain high spectral resolution. G. Meijer et al., *Coherent Cavity Ring Down Spectroscopy*, 217 Chemical Physical Letters 112 (Jan. 1994). Although the authors extended the RDCS technique, they still used a pulsed dye laser.

To date, therefore, only short pulsed radiation sources (such as an excimer pumped dye laser) have been used to implement RDCS. This is because the pioneers of the RDCS technique, O'Keefe and Deacon, expressly required a pulsed radiation source. Pulsed lasers avoided the problem associated with the requirement of longitudinal mode coincidences by using short optical pulses so that every pulse of the laser enters the cavity with no additional intensity fluctuation or time delay. As a result, the sensitivity and data rate improve and the technical requirements of the system are relaxed.

Pulsed lasers are, however, large, bulky, and expensive. Although suitable for laboratory work, they are often impractical for field measurements. Accordingly, there remains an acute need for a relatively inexpensive and reliable device able to measure trace species at levels below 1 ppb by volume in industrial and environmental monitoring applications. The principle object of the present invention is to meet that need.

SUMMARY OF THE INVENTION

To achieve that and other objects, and in view of its purposes, the present invention provides an improved apparatus for trace species detection and measurement in a sample gas. The apparatus includes a ring down cavity cell formed by two highly reflective mirrors aligned along the optical axis of the cell as a near confocal etalon. The sample gas flows through a narrow tube that is coaxial with the optical axis of the ring down cavity cell; therefore, the sample gas fills the ring down cavity cell. A single mode, tunable, continuous wave diode laser having a narrow band emits radiation which is directed to the ring down cavity cell. A temperature controller and a calibration cell help to tune the continuous wave laser to the peak of a predetermined spectral line of the trace species to be detected. A photodetector measures radiation levels resonated by the ring down cavity cell and produces a corresponding signal. The decay rate of the ring down cavity cell is calculated from the signal produced by the photodetector and is used to determine the level of the trace species in the sample gas.

It is to be understood that both the foregoing general description and the following detailed description are exemplary, but are not restrictive, of the invention. In order to make the detailed description more concrete, the focus is on the detection of water vapor. The wavelength of the laser, optics, and photodetector would have be changed, of course, to detect other trace species. The expected sensitivity will scale in direct proportion to a change in the molecular absorption strength of the species of interest.

BRIEF DESCRIPTION OF THE DRAWING

The invention is best understood from the following detailed description when read in connection with the accompanying drawing, in which.

DETAILED DESCRIPTION OF THE INVENTION

Figure 1:
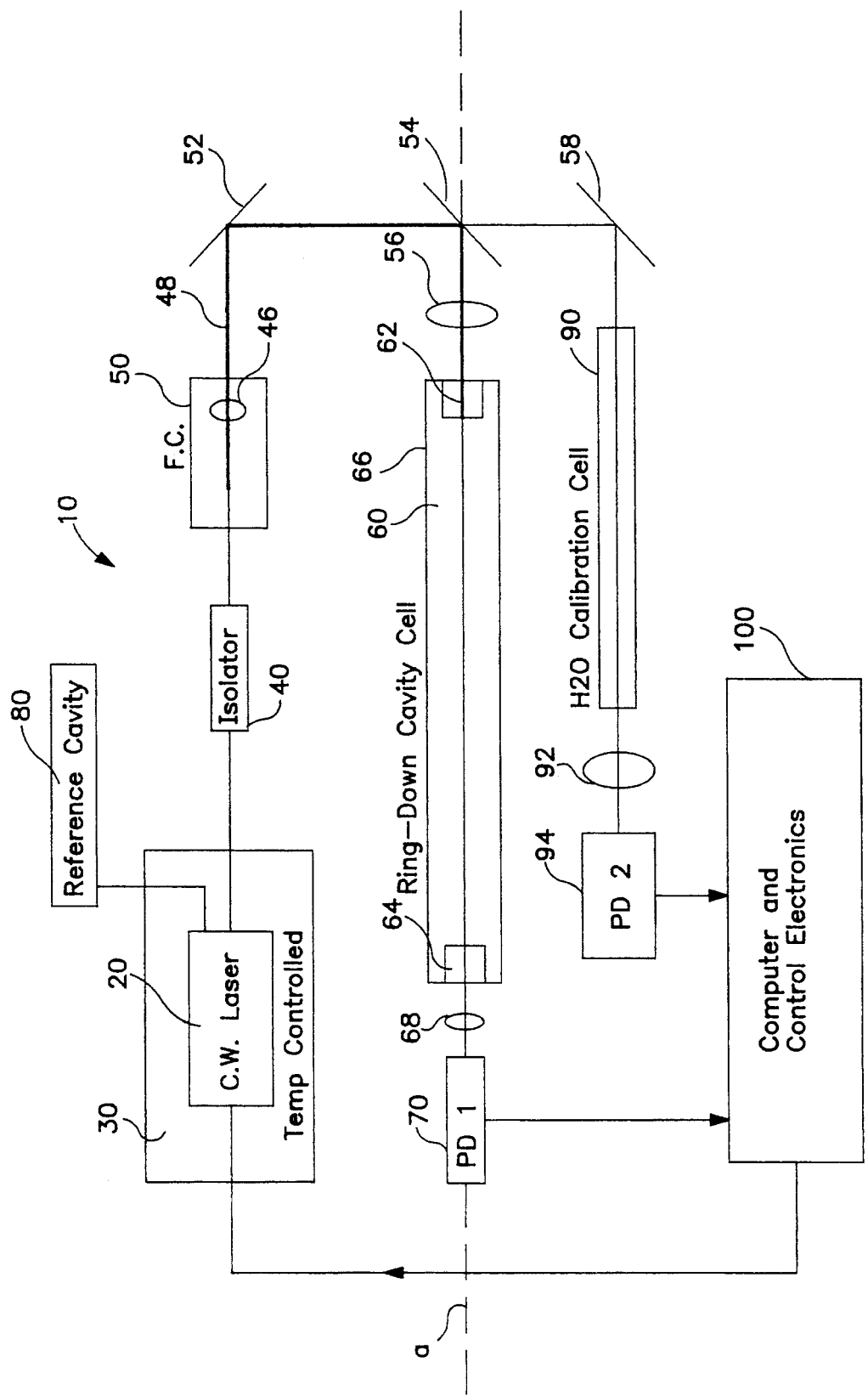
FIG. 1 is a schematic diagram of the apparatus according to the present invention.

Turning to FIG. 1, an apparatus 10 is shown for the detection of water vapor down to the sub-ppb level. Light is generated from a narrow band, tunable, continuous wave diode laser 20. Single mode diode lasers have been produced by SRI International of Menlo Park, Calif. and David Sarnoff Research Center of Princeton, N.J., at a wavelength of 1.39 μm, and have already been commercialized by Sensors Unlimited, Inc. of Princeton, N.J. These lasers can be tuned to lines in the strong first overtone band of water. Preferably, therefore, laser 20 is a single mode, continuous wave diode laser tunable in the wavelength region of 5 nm around 1.393 μm.

Laser 20 may be a distributed feedback (DFB) laser. DFB lasers are one of the most robust types of lasers and constitute a stable, single mode, continuous wave, tunable, diode laser. Recently, "external cavity" diode lasers have become commercially available (from, for example, New Focus). These lasers have an antireflection coating on one facet of the diode laser, preventing it from acting as a laser cavity on its own. Instead, the diode is placed as part of an extended cavity, usually with a grating for wavelength control. Such external cavity lasers are more expensive and less rugged than DFB lasers, but they have a wider spectral coverage and reduced frequency noise (from tens of MHz to about 100 KHz). Laser 20 may be an external cavity laser.

Another type of laser suitable for use as laser 20 in apparatus 10 is an optical fiber laser. Optical fiber lasers are made by doping a metal ion inside an optical fiber and then pumping the ion with a diode laser. Particularly near 1.55 μm, optical fiber lasers have been rapidly developed because they permit direct optical amplification of signals traveling down a fiber. Existing fiber systems require conversion of light to an electrical signal with a photodetector and amplification followed by conversion from electrical energy back to optical energy.

In addition to the practical convenience of an all solid state, compact source of light, a narrow bandwidth diode laser 20 provides superior performance over a pulsed laser for the RDCS method. Using a pulsed dye laser as the excitation source in the RDCS method, a noise equivalent absorption coefficient ($\alpha$) of $7 \times 10^{-10}$ cm$^{-1}$ (0.5 sec integration time) can be achieved in the spectral region near 500 mm. D. Romanini & K. Lehmann, Supra. Using this same sensitivity for the 1.39 μm region using diode laser 20 for excitation, combined with the known strength of the strongest lines in the water spectrum, a sensitivity of 0.7 ppb (2$\sigma$, 0.5 sec integration time) can be obtained for detection of water vapor in one atmosphere of dry air. In addition, as will be shown below, the change from pulsed dye laser to single mode diode laser 20, as well as the change in wavelength, increases the sensitivity of the RDCS method.

Laser 20 is temperature tuned by a temperature controller 30 to put its wavelength on the desired H$_2$O spectral line. Tuning is established by a wavemeter which can measure wavelengths to an accuracy of better than 1 ppm, much less than the width of H$_2$O transitions when pressure broadened by one atmosphere of air (about 10 ppm). In a field-deployable system, a closed cell should be provided that is saturated with water vapor and laser 20 tuned to the peak of the water line by traditional FM spectroscopy.

An isolator 40 is positioned in front of and in line with the radiation emitted from laser 20. Isolator 40 provides a one-way transmission path, allowing radiation to travel away from laser 20 but preventing radiation from traveling in the opposite direction. Thus, isolator 40 protects laser 20 from back reflections or optical feedback, which tend to increase laser noise. Isolators are rated in decibels (db), and isolator 40 preferably has a 60 db rating.

The light emitted from laser 20 must be coupled as efficiently as possible into the optical fiber 48. A single mode fiber coupler (F.C.) 50 is provided for that purpose. Fiber coupler 50 is positioned in front of and in line with isolator 40. Fiber coupler 50 receives and holds optical fiber 48 and directs the radiation emitted from laser 20 toward and through a first lens 46. First lens 46 collects and focuses the radiation. Because the beam pattern emitted by laser 20 does not perfectly match the pattern of light propagating in optical fiber 48, there is an inevitable mismatch loss. Fiber coupler 50 reduces this loss to about 3 db.

The laser radiation is approximately mode-matched into a ring down cavity (RDC) cell 60. A reflective mirror 52 directs the radiation toward a beam splitter 54. Beam splitter 54 directs at least 50%, and typically about 90%, of the radiation through a second lens 56. Second lens 56 collects and focuses the radiation into cell 60. The remaining radiation, typically 10%, passes through beam splitter 54 and is directed by a reflective mirror 58 into a water calibration cell 90—also referred to as a wavelength select meter.

Calibration cell 90 is used to tune laser 20 to the peak of the water line. The radiation which is transmitted through calibration cell 90 is directed toward and through a fourth lens 92. Fourth lens 92 is aligned between calibration cell 90 and a second photodetector 94 (PD 2). The "Noise Equivalent Power," or NEP, of second photodetector 94 is about $10^{-15}$ W. (NEP is a unit used for detection and indicates that amount of light which would produce a signal equal to the "noise" in one second.) Photodetector 94 provides input to computer and control electronics 100.

Cell 60 is made from two, highly reflective mirrors 62, 64, with radii of curvature of about 1 meter and separated by a distance, d, of about 1 meter. This distance was chosen based upon stock available mirrors; shorter cells could easily be built for a field-deployable system with only a modest decrease in sensitivity. Mirrors 62, 64 can be obtained from Research Electropic of Boulder, Colo. The mirrors are aligned as a near confocal etalon along an axis, a. Cell 60 can be pumped at elevated temperature to reduce water vapor absorption.

The length of cell 60, L, is a compromise between opposing requirements. Because RDC decay time is dominated by mirror losses and transmissivity, the cavity length should be maximized. On the other hand, the maximum length is determined by space considerations and by the requirement that the cavity be stable with respect to beam size. According to the theory of stable resonators, in the case of two mirrors with the same radius of curvature, r, the transverse modes of the resonator have a finite size if the cavity length is less than 2 r (their size diverges for this value).

Mirrors 62, 64 constitute the input and output windows of cell 60. The sample gas under study flows through a narrow tube 66 (1 $cm^2$ cross section) that is coaxial with the optical axis, a, of cell 60. Mirrors 62, 64 are placed on adjustable flanges or mounts (not shown) that are sealed with vacuum tight bellows (also not shown) to allow adjustment of the optical alignment of cell 60.

Mirrors 62, 64 have a high-reflectivity dielectric coating and are oriented with the coating facing inside the cavity formed by cell 60. A small fraction of laser light enters cell 60 through front mirror 62 and "rings" back and forth inside the cavity of cell 60. The mechanical alignment of the mirrors is most forgiving when the RDC is close to confocal (L=r) and becomes extremely critical when either the concentric (L=2r) or planar (L is much less than r) limits are approached.

Light transmitted through rear mirror 64 (the reflector) of cell 60 is directed toward and through a third lens 68 and, in turn, imaged onto a first photodetector 70 (PD 1). Like second photodetector 94, the NEP of first photodetector 70 is about $10^{-15}$ W. Photodetectors 70, 94 are thermoelectrically cooled.

Each of photodetectors 70, 94 converts an incoming optical beam into an electrical current and, therefore, provides an input signal to computer and control electronics 100. The most commonly used photodetectors are semiconductor pin photodiodes and avalanche photodiodes. Important detector characteristics are speed of response, spectral response, internal gain, and noise. Because avalanche photodiodes have internal gain, they are preferred for highly sensitive receivers. Ge, AlGaAs, and InGaAs photodiodes are suitable. InGaAs performs better at low signal levels than Ge, because it has smaller values of dark current (i.e., it is less noisy), and is less expensive than AlGaAs. Accordingly, photodetectors 70, 94 are preferably InGaAs.

The input signal represents the decay rate of the cavity ring down. This is measured by attenuating the laser radiation or moving its frequency off resonate with the modes of cell 60. The signal is amplified, digitized by a computer equipped with a transient recorder board, and fitted via a weighted least squares technique to a first order exponential decay curve. The "empty cell" decay rate, τ, can be determined by tuning laser 20 a few molecular linewidths off resonances. This will subtract not only the decay rate caused by the finite reflectivity of the mirrors, but also any broadband absorption features due to other molecular species in the sample. By subtracting the decay rates determined from the average of above and below molecular resonance, a smoothly varying background absorbance can be removed as well. Given the fact that only very small polyatomic molecules have rotationally resolved overtone spectra in the near-IR, this provides a sensitive discrimination against almost any potential source of interference.

Alternatively, the decay rate of the cavity ring down can be extracted using a dual channel gated integrator. This was done by D. Romanini & K. Lehmann, supra.

In describing the operation of the cell, mirrors 62, 64 are assumed to have a transmission (T) of 10 ppm and a combined scattering and absorption loss (L) of 10 ppm, resulting in a reflectivity, R=1−T−L=99.998%. These represent values currently available. Cell 60 has low transmission ($\approx T^2$) except for narrow resonances where the transmission rises to $T/(1R)^2 \approx 0.25$. These resonances are separated in frequency by the "Free Spectral Range" of the etalon (FSR=c/2d=150 MHz, c=speed of light). Each resonance has a Lorentzian lineshape with a full width of half maximum (FWHF), δv, of the FSR divided by the finesse (which is equal to $\pi\sqrt{R}/(1-R)=1.6\times10^5$), thus δv=1 KHz. Radiation inside cell 60 will build-up (when excited by laser 20) and ring-down (when laser 20 is turned off or frequency modulated off the cavity mode) with a time constant τ=d/c(1−R)=167 μs. When a molecular absorber is present in cell 60, the decay of radiation will be increased:

$$I(t)=I(O) \exp(-(1/\tau+c\alpha)t),$$

where α is the absorption coefficient of the gas. Laser 20 is 100% amplitude modulated, giving 2τ for build-up of the light intensity. Following the ringing down of the radiation intensity of 2τ, the cavity ring down is detected at a rate of ¼τ=1.5 KHz.

From the ring-down cavity method, the absorption coefficient, α (v), of the gas contained between mirrors 62, 64 of the cell 60 at a particular frequency, v, is determined. The absorption coefficient is directly proportional to the water concentration. To estimate the minimum detectable water concentration, the noise equivalent absorption coefficient ($\alpha_{min}$) of $7\times10^{-10}$ $cm^{-1}$ (2σ with 0.5 second integration time) is used. That coefficient has already been achieved by D. Romanini & K. Lehmann, supra. Although apparatus 10 can do better than this value, that coefficient is already more than sufficient to achieve 1 ppb detection of water vapor in air.

The strongest rotational line in the 1.39 μm band of water (at 7327.692 cm$^{-1}$=1.3647 μm) has an absorption cross-section ($\sigma^2$) of 3.7×10$^{-20}$ cm$_2$/molecule when at room temperature and broadened by one atmosphere of air (line has a full width at half maximum of 0.18 cm$^{-1}$). Because the absorbance and cross-section are related by $\alpha=N\sigma^2$ where N is the number density using $\alpha_{min}$ above, the minimum detectable number density is calculated to be $N_{min}$=1.9×10$^{10}$ molecules/cm$^3$. At one atmosphere pressure and room temperature, the total number density is equal to 2.69×10$^{19}$ molecules/cm$^3$; thus, the minimum detectable water concentration corresponds to a detection sensitivity of 0.7 ppb. If one found a chance line coincidence with this particular water transition, one could change to one of the other strong lines in the same spectral region. Between 1.36–1.40 μm, there are twelve other transitions with cross-sections within a factor of two of the one used above, thus allowing a detection sensitivity between 0.7 and 1.4 ppb on any of them.

The above sensitivity limit is an experimentally observed noise equivalent absorption coefficient. Consider a comparison between the expected sensitivities for excitation with a short pulsed laser (as has been done previously) and excitation with single mode, continuous wave laser 20 (according to the present invention)—such as a diode laser with the same average power. A first comparison is made for the limit of perfectly coherent excitation; large improvements can be obtained using continuous wave laser 20. Second, a comparison is made given the linewidth of the single mode obtained in the second case, this improvement validates that the sensitivity calculated above will be an underestimate of the capabilities of apparatus 10.

The analysis by D. Romanini & K. Lehmann, supra, showed that the major source of noise arose from shot noise in the number of detected photons. Shot noise is proportional to the square root of the number of detected photons, which for the same detection set-up will be proportional to the square root of the number of photons per second that are injected into cell 60 at the start of each detected cavity decay. This is the quantity compared. The number of photons striking photodetector 70 will be a fraction of T/2(1−R)≈0.25 of this number in both cases.

Consider first excitation by a pulse laser whose pulse width is shorter than the round trip time of the ring-down cavity (c/2d). In this case, no interference can occur and a constant fraction, T, of the pulsed energy is injected into cell 60. If the laser has average intensity, $I_0$, and frequency, ν, the number of injected photons into cell 60 per second is given by $N_{pulsed}$=$I_0$×T÷(hν). Now consider excitation by a perfectly monochromatic laser of the same average power. When exciting an etalon on resonance, in steady state the light intensity inside the etalon will be given by $I_{internal}$=$I_0$×T÷(1−R)$^2$ which for the parameters given above is about 2.5×10$^4$ times higher than the incident light intensity $I_0$.

If the RDC is excited for two decay times, an intensity of about 86% of this steady state value is reached. Thus, at the beginning of each ring down, the number of photons in the cavity will be given by:

$$\# \text{ of photons/decay} = 0.86 \times I_0 \times \frac{T}{(1-R)^2} \times \frac{1}{h\nu} \times \frac{2d}{c}.$$

Given that the ring-down decay time is given by $$\tau = \frac{d}{c(1-R)},$$

and a detection rate of ¼τ decays/second, the number of photons/second injected into cell 60 is given by:

$$N_{monochromatic} = 0.46 \times \frac{I_0}{h\nu} \times \frac{T}{1-R}.$$

Comparing with the above expression, we have for the same average power and laser frequency an improvement of a factor of about ½(1−R), or about 2.5×10$^4$. This translates into over a hundred-fold improvement in signal to noise, and thus detection sensitivity.

The difficulty is that, to coherently excite cell 60, an effective linewidth of laser 20 must be less than the transmission bandwidth of the etalon (δν ≈1 KHz). This is not possible with a simple diode laser with an internal cavity. It is possible, however, to optically lock a diode laser by feedback from an external resonant reference cavity 80—as was first demonstrated by B. Dahmani et al., *Frequency Stabilization of Semiconductor Lasers by Resonant Optical Feedback*, 12 Optics Letters 876 (Nov. 1987). The authors found that, with controlled feedback from a modest finesse (≈100) cavity, the linewidth of diode lasers could be reduced from tens of MHz to a few KHz. In addition, the amplitude noise of the lasers was reduced by over an order of magnitude as well.

Such an optical locking technique will work with a cavity of the high finesse of the ring-down cavity. The technique permits coherent build-up of cell 60 and dramatic improvement of the sensitivity for detection of water vapor concentration down to the few parts-per trillion (ppt) level. Preliminary experimental work has demonstrated such optical locking with an optical cavity with a finesse of ≈10,000, already high enough to make a sensitive apparatus 10.

Consider now the case of excitation with a laser whose width $\Delta\nu_L \gg \delta\nu$, but is still narrow enough that it will only excite a singe mode of the ring-down cavity ($\Delta\nu_L$>FRS). In this case, the steady state intensity inside cell 60 will be given by:

$$I_{internal} = I_0 \times \frac{T}{(1-R)} \times \frac{FSR}{\Delta\nu_L},$$

where FSR=c/2d is the free spectral range of the etalon (150 MHz). Making the same corrections as above we find:

$$N_{finite\ bandwidth} = 0.46 \times \frac{I_0}{h\nu} \times T \times \frac{FSR}{\Delta\nu_L},$$

and, thus, differs from the pulsed excitation result by one-half of the ratio of the etalon free spectral range to the laser linewidth. For the DFB 1.39 μm diodes used, $\Delta\nu_L$≈30 MHz, which is about one-fifth of the FSR. Thus, at the same wavelength and average power, the continuous wave excitation of laser 20 introduces twice the number of photons/second into cell 60 as with conventional short pulsed excitation.

Shot noise dominates over detector noise. With a diode laser linewidth of 30 MHz, the peak fractional transmission of cell 60 is ≈10$^{-4}$, implying an intensity of about 3 μW on photodetector 60. Shot noise for such a light source is about 7×10$^{-13}$ W/(Hz)$^{1/2}$. Because the intrinsic noise in photodetector 70 is about 10$^{-15}$ W/(Hz)$^{1/2}$, shot noise will dominate by several orders of magnitude. In fact, for a detector noise of 10$^{-15}$ W/(Hz)$^{1/2}$, shot noise will dominate for light intensities greater than 6 pW.

Turn now to the effect of changes in the wavelength and average intensity of laser 20. D. Romanini & K. Lehmann, supra, used a laser with ≈1 mJ/pulse operating at 20 Hz, for an average power of 20 mW. The 1.39 μm diode laser already produced by Sensors Unlimited has an output power of 30 mW. In addition, given the longer wavelength, 2.6 as many photons/mW are provided. This corresponds to four times the number of photons/second.

The dye laser used by D. Romanini & K. Lehmann, supra, had poor mode quality which hindered mode matching into cell 60. Consequently, the authors had to delay the sampling of the ring down cavity decay for a few seconds to obtain an exponential decay. That delay lowered the effective input power by an order of magnitude. This problem is avoided by using diode laser 20. At wavelengths near 500 nm, Rayleigh scattering contributed to the loss in cell 60, but given the $\lambda^4$ dependence of the scattering cross-section, this loss mechanism should be less than 2% as important at 1.37 μm.

What is the fundamental limit on the sensitivity that could be achieved by RDCS? D. Romanini & K. Lehmann, supra, showed that, with optimal signal processing, the minimal fractional sample absorption that can be determined from a single decay of the ring down cavity is given by:

$$\sigma_\alpha = \frac{1}{c\tau} \times \left| \frac{h\nu}{QI_{det}\tau} \right|^{1/2},$$

where Q is the quantum efficiency of the detector for InGaAs) and $I_{det}$ is the light intensity on the photodetector at the start of the ring down decay. Using $\tau$=167 μs and $I_{det}$=3 μW, this standard deviation of the absorbance is found to be $\sigma_\alpha$=3.6×10$^{-12}$ cm$^{-1}$. For a signal average at a rate of 1.5 KHz (¼σ), the noise on the absorbance will be reduced by the square root of 1.5 KHz to 1.0×10$^{-14}$ cm$^{-1}$. For the cross-section of the water absorption given above, this corresponds to a detection limit of 2.5×10$^6$ molecules/cm$^3$ which is only 0.1 ppt in a gas at standard conditions. By optical locking the diode laser to cell 60, the transmission of the cavity should increase by about 10$^3$ to ≈3 mW. Shot noise at such a power level would imply a detection sensitivity of 0.003 ppt.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. In addition to detection and measurement of trace water in a sample gas, apparatus 10 of the present invention can be used to detect and measure other trace species. Such species include, but are not limited to, methane, substituted methanes, ethane, ethylene, acetylene (ethyne), benzene, hydrochlorofluorocarbons, formaldehyde, hydrogen chloride, hydrogen fluoride, hydroxyl radical, methyl radical, nitrous oxide, nitrogen dioxide, oxygen, ozone, silane, and germane.

What is claimed is:

1. An apparatus for detection and measurement of trace species in a sample gas comprising:

a ring down cavity cell filled with said sample gas and adapted to resonate radiation, said ring down cavity cell having an optical axis;

a continuous wave laser emitting radiation;

means for directing said radiation emitted from said continuous wave laser to said ring down cavity cell;

a first photodetector measuring radiation levels resonated by said ring down cavity cell and producing a corresponding signal;

means, responsive to said signal from said first photodetector, for calculating the decay rate of said ring down cavity cell; and means, responsive to said decay rate, for determining the level of trace species in said sample gas.

2. The apparatus as recited in claim 1 wherein said continuous wave laser is a tunable diode laser having a narrow band.

3. The apparatus as recited in claim 1 wherein said continuous wave laser is a single mode laser tunable in the wavelength region of 5 nm around 1.39 microns.

4. The apparatus as recited in claim 1 further comprising a temperature controller adapted to tune the wavelength of said continuous wave laser on a predetermined spectral line of the trace species.

5. The apparatus as recited in claim 1 further comprising an isolator positioned between said continuous wave laser and said directing means and in line with the radiation emitted from said continuous wave laser, said isolator minimizing noise in said continuous wave laser.

6. The apparatus as recited in claim 1 wherein said directing means includes:

an optical fiber in which said radiation propagates from said continuous wave laser to said ring-down cavity cell; and a single mode fiber coupler receiving radiation from said continuous wave laser and directing the radiation into said optical fiber.

7. The apparatus as recited in claim 1 wherein said ring down cavity cell includes a front highly reflective mirror and a rear highly reflective mirror, said mirrors aligned along said optical axis of said ring down cavity cell as a near confocal etalon.

8. The apparatus as recited in claim 7 wherein said highly reflective mirrors have radii of curvature of about 1 meter.

9. The apparatus as recited in claim 8 wherein said highly reflective mirrors are separated by a distance of about 1 meter.

10. The apparatus as recited in claim 1 further comprising a narrow tube coaxial with said optical axis of said ring down cavity cell through which said sample gas flows.

11. The apparatus as recited in claim 1 further comprising means for tuning said continuous wave laser to the peak of a predetermined spectral line of the trace species.

12. The apparatus as recited in claim 11 wherein said tuning means includes:

a beam splitter positioned between said continuous wave laser and said ring down cavity cell dividing the radiation into a first beam directed into said ring down cavity cell and a second beam;

a calibration cell receiving said second beam from said beam splitter;

a second photodetector receiving said second beam from said calibration cell and producing a corresponding signal;

computer and control electronics for tuning said continuous wave laser in response to said signal from said second photodetector.

13. The apparatus as recited in claim 1 wherein said first photodetector is InGaAs.

14. The apparatus as recited in claim 1 further comprising a resonant reference cavity adapted to optically lock said continuous wave laser by feedback.

15. The apparatus as recited in claim 1 wherein the trace species is water.

16. An apparatus for detection and measurement of trace species in a sample gas comprising:

a ring down cavity cell filled with said sample gas and adapted to resonate radiation, said ring down cavity cell having an optical axis, a front highly reflective mirror, and a rear highly reflective mirror, said mirrors aligned along said optical axis as an etalon;

a narrow tube coaxial with said optical axis of said ring down cavity cell through which said sample gas flows;

a single mode, tunable, continuous wave laser having a narrow band and emitting radiation;

a temperature controller adapted to tune the wavelength of said laser on a predetermined spectral line wavelength of said laser on a predetermined spectral line of the trace species;

means for tuning said laser to the peak of the predetermined spectral line of the trace species;

means for directing said radiation emitted from said laser to said ring down cavity cell;

a first photodetector measuring radiation levels resonated by said ring down cavity cell and producing a corresponding signal;

means, responsive to said signal from said first photodetector, for calculating the decay rate of said ring down cavity cell; and means, responsive to said decay rate, for determining the level of trace species in said sample gas.

17. The apparatus as recited in claim 16 wherein said laser is tunable in the wavelength region of 5 nm around 1.39 microns.

18. The apparatus as recited in claim 16 further comprising an isolator positioned between said laser and said directing means and in line with the radiation emitted from said laser, said isolator minimizing noise in said laser.

19. The apparatus as recited in claim 16 wherein said directing means includes:

an optical fiber in which said radiation propagates from said laser to said ring-down cavity cell; and a single mode fiber coupler receiving radiation from said laser and directing the radiation into said optical fiber.

20. The apparatus as recited in claim 16 wherein said highly reflective mirrors have radii of curvature of about 1 meter.

21. The apparatus as recited in claim 20 wherein said highly reflective mirrors are separated by a distance of about 1 meter.

22. The apparatus as recited in claim 16 wherein said tuning means includes:

a beam splitter positioned between said laser and said ring down cavity cell dividing the radiation into a first beam directed into said ring down cavity cell and a second beam;

a calibration cell receiving said second beam from said beam splitter;

a second photodetector receiving said second beam from said calibration cell and producing a corresponding signal;

computer and control electronics for tuning said laser in response to said signal from said second photodetector.

23. The apparatus as recited in claim 22 wherein said first and said second photodetectors are InGaAs.

24. The apparatus as recited in claim 16 further comprising a resonant reference cavity adapted to optically lock said laser by feedback.

25. The apparatus as recited in claim 16 wherein the trace species is water.

26. The apparatus as recited in claim 16 wherein said continuous wave laser is a diode laser.

* * * * *